United States Patent [19]

Shachat et al.

[11] 4,012,437
[45] Mar. 15, 1977

[54] METHOD OF PRODUCING BETAINES, MONOMERS AND POLYMERS CONTAINING BETAINE-TYPE UNITS AND NOVEL AND USEFUL COPOLYMERS THEREBY OBTAINED

[75] Inventors: Norman Shachat, Levittown; Richard A. Haggard, Fort Washington; Sheldon N. Lewis, Willow Grove, all of Pa.

[73] Assignee: Rohm and Haas Company, Philadelphia, Pa.

[22] Filed: Feb. 7, 1972

[21] Appl. No.: 224,268

[52] U.S. Cl. .................. 260/482 R; 260/243 B; 260/247.2 R; 260/247.2 B; 260/268 R; 260/326.43; 260/293.87; 260/47 R; 260/486 R; 260/501.13; 526/303; 526/260

[51] Int. Cl.² ............... C07C 101/24; C07C 65/54

[58] Field of Search ....... 260/486 R, 482 R, 243 P, 260/247.2 R, 247.2 B, 326.43, 293.87

[56] References Cited

UNITED STATES PATENTS 2,777,872  1/1957  Shacklett .................... 260/482

FOREIGN PATENTS OR APPLICATIONS 1,487,622  6/1967  France .................... 260/486 R Primary Examiner—Paul J. Killos

[57] ABSTRACT

An improved method is provided for producing polymers of organic compounds, such as ethylenically unsaturated monomers, containing a betaine-type group of the formula:

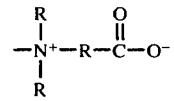

The method involves the reaction of acrylic acid or aqueous methyl acrylate and an aminoalkyl (meth)acrylate or an N-amino-alkyl (meth)acrylamide having a basic tertiary nitrogen atom in the presence of a free radical initiator. The monomers undergo vinyl addition polymerization to form valuable polymers having a wide variety of uses, such as flocculants, retention aids in the deposition of polymers, pigments, etc. on the fibers in a paper pulp, e.g., in the formation of mineral-filled papers.

23 Claims, No Drawings

METHOD OF PRODUCING BETAINES, MONOMERS AND POLYMERS CONTAINING BETAINE-TYPE UNITS AND NOVEL AND USEFUL COPOLYMERS THEREBY OBTAINED

This is a continuation-in-part of our copending application Ser. No. 856,822, filed Sept. 10, 1969, U.S. Pat. No. 3,689,470.

Prior Art

Classical methods for producing betaine-type compounds are by reaction of a tertiary amine with beta-propiolactone (see, for example, Fiedorek, U.S. Pat. No. 2,548,428) and by reaction of a tertiary amine with an α-halo acid salt (see, for example, Schuller et al, U.S. Pat. No. 2,958,682). Toxicity and reagent expense are economically unfavorable in the former and the thermal and pH reaction conditions required for the second method are serious deficiencies for labile reagents.

DESCRIPTION OF THE INVENTION

It is an object of the present invention to provide new methods for producing betaine-type compounds generally, including polymerizable unsaturated types thereof and polymers of the latter. It is an object to provide such a method that utilizes commonly available, relatively nontoxic, and inexpensive starting materials. Another object is to provide a method of this type which does not require high temperatures to attain good yields. Other objects and advantages will be apparent from the description of the invention hereinafter.

While the compounds obtained by the process of the present invention do not all fall within the strict definition of betaines, they can be referred to as of betaine-type by virtue of the quaternary ammonium nitrogen atom which is substituted by a carboxyl-containing radical and the fact that they form an inner salt as is indicated in the formula hereinafter given in equation (A). For convenience, the compounds obtained by the process of the invention may sometimes herein be referred to as a betaine, a betaine-type compound or as an "inner salt of the N-(2-carboxyethyl) quaternary" of the tertiary amine from which the compound is derived; for example, the expression "N-(2-carboxyethyl) inner salt of dimethylaminoethyl acrylate" (DMAEA) may be applied to the product obtained by reaction of acrylic acid with DMAEA.

One method of the present invention involves the reaction of a tertiary amine with acrylic acid according to the following equation:

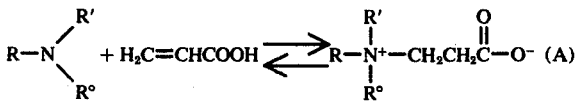

The reaction, insofar as the amine is concerned, is applicable generally to aliphatic and substituted aliphatic amines. The R, R', and R° substituents may be of any aliphatic composition provided they are not reactive otherwise toward the acrylic acid under the conditions prevailing during the betaine-producing reaction. Thus, these substituents may be any alkyl group, cycloalkyl, such as cyclohexyl, aralkyl, such as benzyl, vinylbenzyl, (o, m, or p), alkenyl, such as allyl, hydroxyalkyl, alkoxyalkyl, polyalkoxyalkyl, acryloxyalkyl, acryloxyalkoxyalkyl, acryloxypolyalkoxyalkyl, the corresponding methacryloxy-substituted alkyl and alkoxyalkyl groups and the corresponding acrylamido- or methacrylamido-substituted alkyl and alkoxyalkyl groups. Any two of these three substituents may be joined together to form with the N atom a cyclic group having 5 to 6 atoms (of C, O, S, or N) in the ring, such as morpholino, thiomorpholino, N-alkyl-piperazino and piperidino groups. The size of the various substituents on the N atom of the tertiary amine is limited only by the manifestation of steric hindrance. However, when all three of R, R' and R° are alkyl or aralkyl groups, they may have 1 to 8 carbon atoms, or one of the three may have as many as 24 carbon atoms, provided the other two have not over 8 carbons each and preferably from 1 to 4 carbons in each. One of the three substituents may be a hydroxyalkyl group of 2 to 24 carbon atoms, an alkoxyalkyl group of 3 to 24 carbon atoms, or a poly(alkyloxy)alkyl group having 2 to 6 oxygen atoms and 2 to 3 carbon atoms in all of the alkyl groups except one of the terminal alkyl groups which may have 1 to 8 carbon atoms, preferably 2 to 4. The other two substituents are then preferably alkyl having 1 to 4 carbon atoms. One of the substituents may be one of the groups named above containing an acryloxy, methacryloxy, acrylamido or methacrylamido radical. Such named group may have an alkyl component of 1 to 10 carbon atoms, an alkoxyalkyl component of 3 to 24 carbon atoms, or a poly(alkoxy)alkyl component of the same composition as that designated above for such a group unsubstituted by an acryloxy, methacryloxy, acrylamido, or methacrylamido group. In these cases, also, the other two substituents are preferably ($C_1$–$C_4$)alkyl groups.

In summary, in one preferred group of tertiary amines,
R is ($C_1$–$C_{18}$)alkyl,
R' is ($C_1$–$C_8$)alkyl, and
R° is ($C_1$–$C_8$)alkyl.

In another preferred group of tertiary amines that are adapted to produce polymerizable monomers:
R is a group selected from ($C_1$–$C_8$)alkyl which is substituted by an acryloxy, methacryloxy, acrylamido or methacrylamido group,
R' is ($C_1$–$C_4$)alkyl, and
R° is ($C_1$–$C_4$)alkyl.

The reaction of a tertiary amine and acrylic acid may be carried out without a solvent or in an aqueous or non-aqueous medium. In an aqueous medium, the reaction may be carried out between 0° and about 100° C. at atmospheric pressure. At a given concentration of reactants (tertiary amine and acrylic acid), the equilibrium concentration of betaine increases as the temperature is decreased. However, the rate at which equilibrium is achieved increases with increasing temperature. A preferred temperature range is 10° to 40° C.

The total concentration of acrylic acid and amine in the solvent medium may be anywhere from 5 to 99% by weight and is preferably about 10 to 50% by weight. Generally, a relatively large ratio of acid to amine is preferred in order to favor the shift of the equilibrium toward the formation of the betaine. For practical purposes the ratio of acid to amine is from 0.1:1 to 10:1 and preferably 1:1 to 5:1.

For example, 2.5:1 to 3.5:1 mole ratios can provide equilibrium conversions of amine to betaine as high as 90–95%. In certain cases, the betaine reversal to reactants in Equation (A) is slow enough to permit isolation of the betaine. An appropriate choice of solvent may be used to cause precipitation of the betaine product, further shifting Equation (A) to the right. For most purposes, betaine isolation is unnecessary preparatory to use, the reaction mixture being suitable for direct use, as by polymerization.

As stated above, the range of temperature at which the reaction can be effected is quite wide. Broadly stated, it can be at any temperature above the freezing point of the reaction mixture and below the boiling point of the reaction mixture with a further qualification that when a hydrolyzable amine, i.e., an amine containing a hydrolyzable substituent, such as dimethyl(acetoxyethyl)amine, is used, that the temperature during the reaction is not so high as to hydrolyze the amine extensively. If the medium is basic, hydrolysis of acyloxyalkyl amines is favored. This can be reduced by including sufficient acid to render the medium at least neutral and preferably acid, e.g., a pH of 3–4.5. To limit hydrolysis under these conditions, it is preferred that the ratio of acid to amine be in excess of 1:1.

In the case of the production of polymerizable monomeric betaines, the use of two moles of acrylic acid for each mole of the tertiary amine such as dimethylaminoethyl methacrylate often produces what appears to be a complex of one mole of the betaine with one mole of the acid which often precipitates when the reaction is carried out under anhydrous or essentially anhydrous conditions.

The betaine product may be recovered by any methods well known to workers of average skill in the art.

Another improved method of the present invention is the reaction of the tertiary amine with an acrylic acid ester. Equation (B) represents this reaction:

The two methods mentioned hereinabove are applicable as well to the treatment of polymers containing tertiary amine groups, such as polymers of the N-dialkylaminoalkylamides of acrylic acid or methacrylic acid, especially those in which the alkyl groups contain up to 4 carbon atoms. The methods are applicable also to the analogous polymers containing units formed from dialkylaminoalkyl esters of acrylic acid or methacrylic acid which, as polymeric units, are much less subject to alkaline hydrolysis than the respective monomer. The reaction temperature may be about 0° C. to 100° C., elevated temperatures being preferred. Basic conditions may prevail, when an ester is used. With acrylic acid, neutral to acid pH is used. The polymer reactants contain 1% to 100% of t-amine containing units. The polymers may be prepared in any way, such as by solution, emulsion, bulk, or suspension polymerization techniques.

The betaines produced are known products useful for various purposes in industry and commerce. Especially advantageous products are those containing a polymerizable group such as a vinyl, allyl, acryloxy, methacryloxy, acrylamido, or methacrylamido group therein. Polymers of such products find use as flocculants, pigment retention aids in the mineral filling of paper and soil release treatments for textiles as described in a copending application having a common assignee Ser. No. 7268, filed Jan. 30, 1970 now U.S. Pat. No. 3,671,305.

While excess acrylic acid or methyl acrylate in the products obtained may be removed, nevertheless, for many purposes there is no necessity to remove the excess acid or acrylate ester from the polymerizable monomeric betaine since the acrylic acid or ester copolymerizes with the betaine to produce desirable

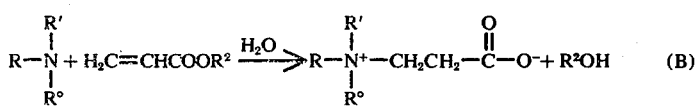

(B)

This reaction requires water. The betaine product is not in equilibrium with the starting alkyl acrylate but is subject to reversal to acrylic acid as in Equation A. The reaction occurs at room temperature although the range of temperature may be from as low as 0° C. up to about 100° C. and preferably in the range of 10°–40° C. The same amines as those mentioned in connection with the method using acrylic acid, which are free of functional groups susceptible to hydrolysis under basic conditions, can be used in this method. When water is the solvent medium, the same conditions of temperature, concentration of acrylic acid ester and amine and relative proportions of the latter two reactants may be used as in the reaction involving acrylic acid instead of the ester. When the solvent medium is a mixture of water and a water-miscible solvent the amount of water should be at least about 1% of the total weight of the ester and the amine and preferably is at least about 10% of such total weight.

The method using acrylic acid has specific advantages when it is desired to produce monomeric betaines from hydrolyzable tertiary amines which are adapted to produce polymerizable betaine-type monomers, such as those tertiary amines in which one of the R groups is an acryloxy- or methacryloxy-substituted alkyl group or the like.

products of polymeric character useful for similar purposes such as for flocculation, anchoring of polymers to the fibers of paper pulp, pigment retention aids in the formation of mineral filled papers and the like.

To assist those skilled in the art to practice the present invention, the following modes of operation are suggested by way of illustration, parts and percentages being by weight and the temperature in ° C. unless otherwise specifically noted.

1. Reaction of Acrylic Acid (AA) and β-N,N-Dimethylaminoethyl Methacrylate (DMAEMA).

A. In aqueous solution

A solution of 72 parts DMAEMA, 33 parts AA (1:1 molar ratio DMAEMA:AA) and 0.5 part p-methoxyphenol (MEHQ) in 245 parts $H_2O$ is stirred at 25° C. Periodically, samples are removed and analyzed by titration for betaine formation. Betaine is determined by the decrease in amine titer. The equilibrium mixture containing about 11 parts DMAEMA, about 5 parts AA and about 86 parts of the N-(2-carboxyethyl) inner salt of DMAEMA is achieved in about 25 days. The pH of the product mixture is 5.1. Thus, the conversion of amine to betaine at equilibrium under the above conditions is about 85%. Other experiments carried out in similar fashion are summarized in the following table:

TABLE I

| Run No. | Starting Materials (parts) DMAEMA | AA | Water | MEHQ | Molar Ratio AA: DMAEMA | T (°C.) | Product Composition (parts) at Eq. DMAEMA | AA | Betaine | Approx. Time to Achieve Eq. (hr.) | Conv. of Amine to Betaine at Eq. (%) | pH at Eq. |
|---|---|---|---|---|---|---|---|---|---|---|---|---|
| 1 | 72.0 | 16.5 | 245 | 0.5 | 0.5 | 80 | (41.8)[a] | 1.7 | 45.0 | 7 | 42 | (4.8)[a] |
| 2 | 72.0 | 33.0 | 245 | 0.5 | 1.0 | 80 | 27.4 | 12.6 | 65.0 | 2 | 62 | 5.2 |
| 3 | 72.0 | 99.0 | 245 | 0.5 | 3.0 | 80 | 14.7 | 72.7 | 83.6 | <2 | 79.5 | 3.4 |
| 4 | 72.0 | 33.0 | 245 | 0.5 | 1.0 | 60 | 19.2 | 8.8 | 77.0 | 7–24 | 73.3 | 5.0 |
| 5 | 412 | 188 | 400 | — | 1.0 | 25 | 55.2 | 24.5 | 520.3 | 600 | 86.6 | 6.3 |
| 6 | 144 | 132 | 490 | — | 2.0 | 25 | 6.5 | 69.0 | 200.5 | <120 | 95.8 | 4.0 |
| 7 | 72.0 | 99.0 | 245 | 0.5 | 3.0 | 25 | 1.7 | 66.8 | 102.5 | 70 | 97.6 | 3.6 |
| 8 | 72.0 | 99.0 | 245 | 0.5 | 3.0 | 60 | 8.2 | 69.8 | 93.0 | 4 | 88.6 | 3.6 |
| 9 | 72.0 | 99.0 | 245 | 0.5 | 3.0 | 40 | 4.1 | 67.8 | 99.1 | 24 | 94.3 | 3.6 |
| 10 | 144 | 198 | 490 | — | 3.0 | 25 | 0.0 | 132 | 210 | <120 | 100 | 3.5 |
| 11 | 157 | 288 | 555 | — | 4.0 | 25 | 0.0 | 216 | 229 | <120 | 100 | 4.0 |

[a]Titration shows that a portion of the DMAEMA is hydrolyzed to methacrylic acid and β-N,N-dimethylaminoethanol.

B. In nonaqueous solution

A mixture of 36 parts DMAEMA and 33 parts AA (1:2 mol ratio) is prepared at 0° and stirred at 25°. Periodically, samples are removed and analyzed by titration for betaine formation. At the end of 2.5 hours, the mixture contains 26 parts of the N-(2-carboxyethyl) inner salt of DMAEMA (greater than 50% amine conversion). The equilibrium mixture after ~20 hours contains about 39 parts betaine (the inner salt referred to), 9 parts DMAEMA and 21 parts AA. With seeding the mixture could be induced to precipitate greater than 75% yields of a 1:1 mol ratio betaine/AA complex. Other experiments are carried out in similar fashion with larger DMAEMA ratios and all reach equilibrium within 20–24 hours.

2. Reaction of (AA) or Methyl Acrylate (MA) and N-Dimethylaminoethanol (DMAE).

A. Anhydrous with AA

A solution of 35.6 parts DMAE and 28.8 parts AA in 200 parts 1,2-dimethoxyethane is prepared at 25°, and warmed to 70°. Within 15 minutes, crystals of product form; the mixture is set aside for 3 days at 25° and filtered, washed with 10° C. dimethoxyethane and the filter cake dried to yeild 40-42 parts of betaine (the N-(2-carboxyethyl) inner salt of DMAE), an hygroscopic white solid of m.p. 120°–122°. Further standing of the mother liquor for several days yielded another 6–8 parts of the betaine, raising the total isolated yield to 71–75% of betaine.

B. In aqueous solution with MA 17.8 parts β-N,N-dimethylaminoethanol (DMAE) and 17.2 parts methyl acrylate are diluted to a total of 500 parts with water. The mixture is kept at room temperature (~25° C.). Aliquots are periodically removed and titrated to determine the amount of betaine formed. The results are as follows:

TABLE II

| Time (min.) | pH of Reaction Mixture | Titer Carboxylic Acid Meq./g. of soln. | pK$_a$ | Amine Meq./g. of soln. | pK$_a$ | % Conv. of Amine to Betaine |
|---|---|---|---|---|---|---|
| 0 | 10.5 | (0.00) | — | (0.400) | — | — |
| 5 | 10.3 | 0.107 | 3.6 | 0.308 | 9.2 | 23.0 |
| 100 | 9.5 | 0.336 | 3.5 | 0.123 | 9.3 | 69.2 |
| 265 | 9.1 | 0.346 | 3.5 | 0.089 | 9.3 | 77.7 |
| 425 | 8.9 | 0.372 | 3.5 | 0.080 | 9.2 | 80.0 |
| 1465 | 8.3 | 0.358 | 3.5 | 0.072 | 9.3 | 82.0 |
| 5800 | 7.2 | 0.392 | 3.5 | 0.069 | 9.3 | 82.7 |

The results show that about 83% of the amine is converted to betaine and that most of the remaining methyl acrylate is hydrolyzed to methanol and AA.

3. Reaction of Poly (DMAEMA) and (MA)

A solution consisting of 150 parts DMAEMA (1 mole), 30 parts Triton X-405 (t-octylphenoxypoly(3-9)ethoxyethanol), 0.005 parts FeSO$_4$·7H$_2$O and 649.3 parts water is cooled to 15° C. and a solution of 0.6 parts ammonium persulfate in 10 parts water is added. The heat of polymerization carries the temperature to about 25° C. within 45 minutes. Polymerization is completed by addition of 0.1 part ammonium persulfate in 5 parts water, three times at 1-hour intervals. The polymer solution exhibits the following properties: % Total Solids (T.S.), 17.2; Titer, 1.13 meq./g. of solution (pK$_a$=7.1).

To the polymer solution there is added 150 parts (approximately 2 moles) methyl acrylate. The properties of the solution are followed on storage at room temperature as follows:

TABLE III

| Time (days) | % T.S. | pH | Brookfield Visc. 60 rpm (cps.) | Amine Titer (Meq./g. of Soln.) | pK$_a$ | % Amine Converted to Betaine |
|---|---|---|---|---|---|---|
| 0 | 14.7 | 8.95 | 920 | 0.933 | 7.4 | 2.3 |
| 2 | 16.4 | 8.0 | 1508 | 0.375 | 7.3 | 60.7 |
| 7 | 17.1 | 7.1 | 2780 | 0.125 | — | 86.9 |
| 10 | 17.7 | 6.7 | 2820 | 0.100 | 7.6 | 89.5 |
| 22 | 17.7 | 6.0 | 2570 | 0.100 | 7.9 | 89.5 |

4. Reaction of Poly (DMAEMA) and (EA)

Procedure 3) above involved a ratio of MA to DMAEMA of about 2. This procedure is repeated changing the ratio to 1.0. After 3 days 63.3% of the amine in the polymer is converted to betaine. After 11 days 76.4% is so converted, and after 65 days 81.2% is so converted. When the same procedure is carried out but with the ratio lowered to 0.5, 37.5% of the amine is converted to betaine after 3 days, and 43.7% is converted after 11 days.

When the same procedure is carried out except that ethyl acrylate (EA) is used with a mole ratio of EA to DMAEMA in the polymer of 1.0, 52.2% of the amine is converted to betaine after 7 days, 64.5% is converted after 13 days, and 82.8% is converted after 97 days. When this procedure is repeated but using a lower ratio of 0.5, 38.7% of the amine is converted to betaine after 7 days, 44.2% is converted after 13 days, and 45.7% is converted after 97 days.

When procedure (3) is repeated but replaceing the methyl acrylate with butyl acrylate (BA) at a mole ratio of 1.0 instead of about 2, 18.4% of the amine is converted to betaine after 7 days, 20.2% is converted after 13 days, and 49.9% is converted after 97 days. At a lower mole ratio of 0.5, somewhat lower conversions are obtained in corresponding times. For example, 44.3% of the amine is converted to betaine after 97 days.

5. Poly(DMAEMA) solutions prepared as in 3) above are separately mixed with AA in the ratios given in Table IV which in the second column gives the pH values of the resulting mixtures at 25° C. The reactions are carried out at the temperatures indicated in the Table and the proportion of DMAEMA units converted to betaine units at certain times are noted.

TABLE IV

| Wt. Ratio AA/polyDMAEMA | Solution pH (25°) | Reaction Temperature | % Conversion in (Time) |
| --- | --- | --- | --- |
| 0.64:1 | 4.7 | 60° | 53% (20 hrs.) |
| 0.46:1 | 5.6 | 60° | 49% (18–20 hrs.) |
| 0.64:1 | 4.7 | 23–25° | 74% (50–60 days) |
| 0.46:1 | 5.6 | 23–25° | 61% (50 days) |

6. A mixture of 100 parts DMAEMA, 100 parts (excess) MA 20 parts Triton X-405, 0.005 parts $FeSO_4 \cdot 7H_2O$ and 759.3 parts water is treated with a solution of 0.6 parts ammonium persulfate in 10 parts water at 25° C. Polymerization occurs slowly as indicated by a rise in temperature and an increase in viscosity. After about an hour, four catalyst changes, each consisting of 0.1 part ammonium persulfate in 5 parts water, are added at about half hour intervals. On storage at room temperature, the mixture undergoes the following changes in properties indicative of reaction of poly(DMAEMA) with MA to give polymer-containing betaine functionality.

TABLE V

| Time (days) | Appearance | % T.S. | pH | Brookfield Visc. 60 rpm (cps.) | Amine Titer (Meq./g. of Soln.) | pK$_a$ | % Amine Converted to Betaine |
| --- | --- | --- | --- | --- | --- | --- | --- |
| 0 | Opaque | 14.6 | 8.7 | 1380 | 0.491 | 7.3 | 22 |
| 1 | Hazy | — | — | — | 0.357 | 7.3 | 43.3 |
| 5 | Clear | 16.2 | 7.6 | 6730 | 0.197 | 7.5 | 68.8 |
| 8 | Clear | — | 7.4 | — | 0.167 | 7.7 | 73.5 |
| 22 | Clear | 16.2 | 6.4 | 7750 | 0.142 | 7.7 | 77.5 |

In similar experiments with ethyl acrylate, about 30% betaine formation occurs in thirteen days.

7. (a) A mixture of 475 parts acrylic acid, 345 parts DMAEMA and 1180 parts $H_2O$ is allowed to react at room temperature. Within 96 hours all of the amine is converted to betaine, giving an aqueous solution containing 61.4% betaine and 38.6% acrylic acid. This solution is used to prepare a polymer as follows:

b. 293 parts of the betaine/AA solution obtained in (a) above, 544.8 parts $H_2O$, 15 parts concentrated $H_2SO_4$, 80 parts MA, 6 parts sodium isodecylphenoxypoly(40)ethoxy sulfate and 0.01 part $FeSO_4 \cdot 7H_2O$ are mixed at room temperature (Co. 23° C.). The temperature of the mixture is adjusted by heating to about 30° C. Polymerization is initiated by addition of 0.4 part ammonium persulfate (APS) dissolved in 10 parts water followed by 0.4 part sodium hydrosulfite (SHS) dissolved in 10 parts water. The heat of polymerization carries the temperature to 61° C. in about 1 hour. About 20 minutes after the peak temperature is reached, 0.1 part APS in 10 parts water and 0.1 part SHS in 10 parts water are added separately. About 15 minutes later 0.1 part APS in 10 parts water and 0.1 part SHS in 10 parts water are added separately again. The dispersion is cooled to 25° C. and the pH is adjusted from 2.1 to 5.8 with 136 parts of 25% aqueous sodium hydroxide. The hazy viscous product contains a copolymer of about 40% MA, 23.2% acrylic acid, and 36.8% of N-(2-carboxyethyl)inner salt of DMAEMA and exhibits the following properties: % T.S. - 20.8 (conversion to polymer about 94%), Viscosity - 11,400 cps.

C. In similar fashion (to part b) the following copolymers are prepared:

TABLE VI

| Composition (wt. %) | % T.S. | % Conv. to Polymer | pH | Viscosity (cps) |
| --- | --- | --- | --- | --- |
| 20MA/49.1 Betaine/30.9AA | 21.4 | 95.0 | 4.5 | 17,600 |
| 60MA/24.6 Betaine/15.4AA | 20.7 | 95.0 | 6.0 | 3,600 |
| 50MMA/36.5 Betaine/12.4AA/ 1.1 DMAEMA | 21.5 | 96.9 | 2.0* | 670 |
| 40EA/43.8 Betaine/14.9AA/ 1.3 DMAEMA | 21.0 | 93.4 | 1.8* | 840 |
| 61.4 Betaine/38.6 AA | 21.6 | 95.0 | 4.7 | 34,000 |

*pH is not post-adjusted with 25% NaOH.

8. An emulsion is prepared from the following ingredients: 488 parts betaine/AA solution prepared in 7)a) above, 12 parts sodium isodecylphenoxypoly(40)ethoxy sulfate, 24 parts concentrated $H_2SO_4$, 190 parts $H_2O$, 200 parts methyl acrylate and 0.8 part ammonium persulfate. A solution of 0.02 part $FeSO_4\cdot 7H_2O$ in 973.6 parts $H_2O$ is heated to 62° C. With stirring the above emulsion is added gradually ca 15 parts per minute) during a period of about 1 hour while the temperature is maintained at 62° C. by the heat of polymerization. As a separate feed, a solution of 0.8 part sodium metabisulfite in 30 parts water is added simultaneously (0.5 part per minute). About 25 minutes after the addition, a solution of 0.2 part APS in 20 parts $H_2O$ and a solution of 0.2 g. sodium hydrosulfite in 20 parts $H_2O$ are added separately. About 15 minutes later the preceding step is repeated. The batch is cooled to 25° C., filtered through cheesecloth and packaged. The dispersion contains a copolymer of about 50% MA, 19.3% AA, and 30.7% betaine (N-(2-carboethoxy) inner salt of DMAEMA)and displays the following properties:

| | |
|---|---|
| $ T.S. | 20.4 |
| % Conversion to polymer | 94.9 |
| pH | 2.1 |
| Viscosity (cps) | 550 |

9. 79 parts AA (MEHQ inhibited) and 135 parts benzyldimethylamine (mole ratio of 1.1 AA:1 amine) are mixed at 0° under a dry nitrogen atmosphere and the homogeneous mixture is brought to 25 ± 2°. Within several hours a viscous precipitate of betaine(N-(2-carboxyethyl)inner salt of benzyldimethylamine), complexed with excess AA, precipitates from the mixture. The small amount of acid-depleted, mobile supernatant liquid after 65 hours is essentially pure benzyldimethylamine. Aliquots of the reaction mixture are removed periodically, treated with a known amount of excess aqueous HCl and potentiometrically titrated. Table VII summarizes the titration data.

TABLE VII

| Aliquot, 0.9 g. | Reaction Time (Hrs. at 25° C.) | Meq. Amine Present (% of Starting Amine) | Approximate Mole Ratio of Carboxylic Acid:Amine |
|---|---|---|---|
| No. 1, homogeneous | <0.25 | 3.50 (83%) | 1.2 |
| No. 2, stirred slurry | 17 | 2.7 (64) | 1.6 |
| No. 3, stirred slurry | 41 | 2.2 (52) | 1.9 |
| No. 4, crude precipitate | 65 and 160 | 1.5 (36) | 3.3 |
| No. 5, decantate | 65 and 160 | 6.5 (—) | ca. 0.1 |

10. The same parts by weight as in 9) above are mixed in 500 parts ice water and the resulting clear solution divided into two portions, one maintained at 60 ± 3° and the second at 25 ± 2°. Homogeneous aliquots are removed periodically and titrated as described above. Table VIII summarizes the titration data. Equilibrium is established in about 5 hours at 60° (60% conversion) and about 12–15 days at 25° (80% conversion).

TABLE VIII

| Aliquot, 3.60 g. | Reaction Time Hrs. (T° C.) | Meq. Amine Found (% of starting amine) | In situ Conversion to Betaine (%) |
|---|---|---|---|
| 1 | <0.25 (25°) | 4.6 (92) | 8% |
| 2 | 1.5 (60°) | 2.9 (58) | 42 |
| 3 | 3.5 (60°) | 2.2 (44) | 56 |
| 4 | 4.5 (60°) | 2.0 (40) | 60 |
| 5 | 4.5 (60°) + 16 (25°) | 1.8 (36) | 64 |
| 6 | 20 (25°) | 2.8 (56) | 44 |
| 7 | 140 (25°) | 1.2 (24) | 76 |
| 8 | 360 (25°) | 1.0 (20) | 80 |

11. 79 parts AA and 101 parts n-butyldimethyl amine (mole ratio 1.1 AA:1.0 amine) are mixed at 0° and the homogeneous mixture brought to room temperature. A solid precipitate appears in increasing amount within several hours. After 48 hours, the mixture is a semisolid paste showing greatly decreased amounts of titrable amine (Table IX). The white, highly hygroscopic betaine (N-(2-carboxyethyl)inner salt of butyldimethylamine) is recrystallized from dry acetone (m.p. 111°–114°); titration shows no amine to be present and a strong carboxylic acid curve of pKa about 3.6.

TABLE IX

| Aliquot, 0.90 g. | Reaction Time, Hrs. (25°) | Meq. Amine (% of Starting Amine) |
|---|---|---|
| No. 1, homogeneous | <0.25 | 4.7 (94%) |
| No. 2, stirred slurry | 18 | about 3 (about 60) |
| No. 3, paste | 43 | 3.0 (60) |
| No. 4, semi-solid | 160 | 1.7 (34) |
| No. 5, recrystallized betaine | (160) | 0 |

12. The same parts by weight of acid and amine as in procedure 11) are mixed in 500 parts ice water and the resulting clear solution divided into two portions, one maintained at 60 ± 3° and the second at 25 ± 2°. Homogeneous aliquots are removed periodically and titrated (Table X). Equilibrium is established in 5–6 hours at 60° (about 50% conversion) and about 12–15 days at 25° (about 70% amine conversion).

TABLE X

| Aliquot, 3.40 g. | Reaction Time, Hrs. (T° C.) | Approximate Meq. Amine Found (% of Starting Amine) | In situ Conversion to Betaine (%) |
|---|---|---|---|
| No. 1 | <0.25 (25°) | 5 (100%) | 0 |
| No. 2 | 1.5 (60°) | 3.8 (76) | 24 |
| No. 3 | 3.5 (60°) | 3.0 (60) | 40 |
| No. 4 | 4.5 (60°) | 2.6 (52) | 48 |
| No. 5 | 4.5 (60°) + 16 (25°) | 2.4 (48) | 52 |
| No. 6 | 20 (25°) | 3.4 (68) | 32 |
| No. 7 | 140 (25°) | 1.9 (38) | 62 |
| No. 8 | 360 (25) | 1.5 (30) | 70 |

13. 150 parts of AA (inhibited by MEHQ) is mixed with 50 parts of N-(diethylaminoethyl)-acrylamide and the mixture is heated to 90° C. and maintained at that temperature for 25 hours, producing the corresponding betaine type compound, namely, the N-(2-carboxyethyl)inner salt of N-(diethylaminoethyl)acrylamide.

14. 75 parts of inhibited AA is mixed with 60 parts of allyldibutylamine and the mixture is heated to 45° C. and maintained at that temperature for 45 hours, with the production of the N-(2-carboxyethyl)inner salt of allyldibutylamine.

15. 65 parts of inhibited AA is mixed with di(methoxyethyl)vinyl amine and allowed to react at 30° C. for 96 hours, thereby producing the N-(2-carboxyethyl)inner salt of di(methoxyethyl)vinyl amine.

16. 150 parts of inhibited AA is mixed with 60 parts of N-dibutylaminopropyl-methacrylamide. The mixture is heated to 50° C. and maintained at that temperature for 30 hours, thereby producing the N-(2-carboxyethyl)inner salt of N-dibutylaminopropyl-methacrylamide.

17. The N-(2-carboxyethyl)inner salt of diethanolmethylamine is obtained by heating a mixture of 70 parts of inhibited AA and 65 parts of diethanolmethylamine at 35° for 72 hours.

18. The N-(2-carboxyethyl)inner salt of cyclohexyldimethylamine is produced by heating a mixture of 70 parts of inhibited AA and 65 parts of cyclohexyldimethylamine at 40° for 60 hours.

19. The N-(2-carboxyethyl)inner salt of hydroxyethoxyethyldiethylamine is produced by heating a mixture of 70 parts of inhibited AA and 65 parts of hydroxyethoxyethyldiethylamine at 40° for 60 hours.

20. 80 parts of inhibited AA is mixed with 85 parts of poly(20)ethoxyethyldipropylamine. The mixture is heated to 65° and maintained at that temperature for 24 hours with the production of the N-(2-carboxyethyl)inner salt of poly(20)ethoxyethyldipropylamine.

21. the N-(2-carboxyethyl)inner salt of dimethylaminoethoxyethyl methacrylate is obtained by heating a mixture of 125 parts of inhibited AA and 175 parts of dimethylaminoethoxyethyl methacrylate at room temperature for 5 days.

22. 75 parts of inhibited AA is mixed with 85 parts of morpholinoethyl methacrylate and the mixture is heated to 45° C. and maintained at that temperature for 45 hours, with the production of the N-(2-carboxyethyl) inner salt of morpholinoethyl methjaxrylate of the formula

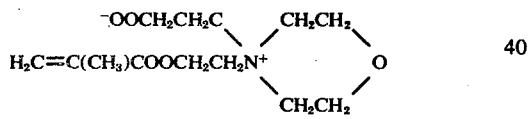

23. 75 parts of inhibited AA is mixed with 85 parts of piperidinoethyl methacrylate and the mixture is heated to 45° C. and maintained at that temperature for 45 hours, with the production of the N-(2-carboxyethyl) inner salt of piperidinoethyl methacrylate of the formula

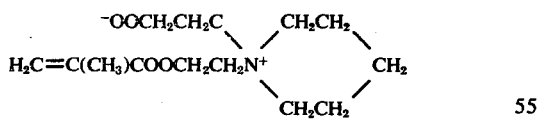

We claim:
1. A method for producing a betaine-type product which comprises reacting, at a temperature of about 0° C. to about 100° C.,
1. acrylic acid with a tertiary amine of the formula

wherein R is ($C_1$-$C_{24}$) alkyl, allyl, benzyl, vinylbenzyl, hydroxyalkyl having 2 to 24 carbon atoms, ($C_1$-$C_8$)-alkyl substituted by an acryloxy, methacryloxy, acrylamido or methacrylamido, alkoxyalkyl having 3 to 24 carbon atoms, or a poly(alkoxy)alkyl group having 2 to 6 oxygen atoms and 2 to 3 carbon atoms in all except one of the terminal alkyl groups, the latter having 1 to 8 carbon atoms; R' is a ($C_1$-$C_8$) alkyl group; R° is a ($C_1$-$C_8$) alkyl group, or R' and R° may be joined together and form with the N atom of the tertiary amine, a ring selected from morpholino, thiomorpholino, N-alkylpiperidino, or piperazino or 2. acrylic acid with a polymer containing tertiary amine groups, of the formula above where R is ($C_1$-$C_8$) alkyl substituted by acryloxy, methacryloxy, acrylamido or methacrylamido, and R' and R° are as defined above, or 3. acrylic acid with a mixture of a tertiary amine as defined in (2) and (b) a polymer of said tertiary amine, the molar ratio of acid to amine in the mixtures (1), (2), and (3) being from 0.1:1 to 10:1.

2. A method according to claim 1 in which the molar ratio of acid to amine is about 1:1 to 5:1.

3. A method for producing a betaine-type product which comprises reacting, in an aqueous medium at a temperature of about 0° to about 80° C.
acrylic acid with a tertiary amine of the formula,

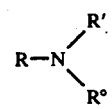

wherein R is ($C_1$-$C_{24}$) alkyl, allyl, benzyl, vinylbenzyl, hydroxyalkyl having 2 to 24 carbon atoms, ($C_1$-$C_8$) alkyl substituted by an acryloxy, methacryloxy, acrylamido or methacrylamido, alkoxyalkyl having 3 to 24 carbon atoms, or a poly(alkoxy)alkyl group having 2 to 6 oxygen atoms and 2 to 3 carbon atoms in all except one of the terminal alkyl groups, the latter having 1 to 8 carbon atoms; R' is ($C_1$-$C_8$) alkyl; R° is ($C_1$-$C_8$) alkyl, or R' and R° may be joined together and form with the N atom of the tertiary amine, a ring selected from morpholino, thiomorpholino, N-alkylpiperidino, or piperazino.

4. A method for producing a betaine-type product which comprises reacting, in an aqueous medium at a temperature of about 0° to about 80° C.,
1. acrylic acid, with a polymer containing tertiary amine groups of the formula

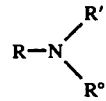

wherein R is ($C_1$-$C_8$) alkyl substituted by an acryloxy, methacryloxy, acrylamido or methacrylamido R' and R° are ($C_1$-$C_8$) alkyl, or R' and R° are joined together with the N atom to form morpholino, thiomorpholino, N-alkylpiperidino or piperzino or 2. acrylic acid with a mixture of (a) a tertiary amine of the formula as defined above in (1) and (b) a polymer of said teritary amine, the molar ratio of acid to amine being from 0.1 to 10:1.

5. A method according to claim 1 in which the reaction is effected at a temperature of about 10° C. to 40° C.

6. A method for producing a betaine-type product which comprises reacting, at a temperature of about 0° C. to about 100° C., acrylic acid with a tertiary amine of the formula

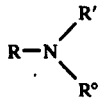

wherein R is $(C_1-C_{24})$ alkyl, allyl, benzyl, vinylbenzyl, hydroxyalkyl having 2 to 24 carbon atoms, $(C_1-C_8)$-alkyl substituted by an acryloxy, methacryloxy, acrylamido or methacrylamido, alkoxyalkyl having 3 to 24 carbon atoms, or poly(alkoxy)alkyl having 2 to 6 oxygen atoms and 2 to 3 carbon atoms in all except one of the terminal alkyl groups, the latter having 1 to 8 carbon atoms; $R'$ is $(C_1-C_8)$ alkyl; $R°$ is a $(C_1-C_8)$ alkyl group, or $R'$ and $R°$ may be joined together and form with the N atom of the tertiary amine, a ring selected from morpholino, thiomorpholino, N-alkylpiperidino, or piperazino.

7. A method according to claim 1

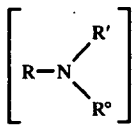

wherein R is $(C_1-C_8)$ alkyl substituted by acryloxy, methacryloxy, acrylamido or methacrylamido, $R'$ is $(C_1-C_4)$ alkyl, and $R°$ is $(C_1-C_4)$ alkyl.

8. A method according to claim 1 in which the tertiary amine is dimethylaminoethyl acrylate dimethylaminoethyl methacrylate, N-dimethylaminoethyl acrylamide or N-dimethylaminoethyl methacrylamide or a polymer containing units thereof.

9. A method according to claim 3 in which the reaction is effected at a temperature of about 10° C. to 40° C.

10. A method according to claim 3 wherein R is $(C_1-C_8)$ alkyl substituted by acryloxy, methacryloxy, acrylamido or methacrylamido; $R'$ is $(C_1-C_4)$ alkyl and $R°$ is $(C_1-C_4)$ alkyl.

11. A method according to claim 3 wherein the tertiary amine is dimethylaminoethyl acrylate, dimethylaminoethyl methacrylate, N-dimethylaminoethyl acrylamide or N-dimethylaminoethyl methacrylamide or a polymer containing said amines.

12. A process according to claim 3 for preparing a betaine-type product having the formula

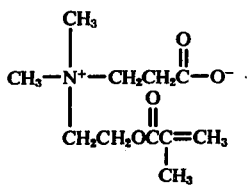

which comprises reacting acrylic acid with β-N, N-dimethylaminoethyl methacrylate at 25° C.

13. A method for producing a betaine-type product which comprises reacting, in an aqueous medium at a temperature of about 0° to about 80° C., a lower alkyl ester of acrylic acid with a tertiary aliphatic amine of the formula

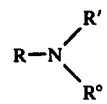

wherein R is $(C_1-C_{24})$ alkyl, allyl, benzyl, vinylbenzyl, hydroxyalkyl having 2 to 24 carbon atoms, a $(C_1-C_8)$ alkyl substituted by an acryloxy, methacryloxy, acrylamido or methacrylamido group, alkoxyalkyl having 3 to 24 carbon atoms in all except one of the terminal alkyl groups, the latter having 1 to 8 carbon atoms; $R'$ is $(C_1-C_8)$ alkyl; $R°$ is $(C_1-C_8)$ alkyl, or $R'$ and $R°$ may be joined together and form with the N atom of the tertiary amine, a ring selected from morpholino, thiomorpholino, N-alkylpiperidino, or piperazino.

14. A method according to claim 13 wherein R is $(C_1-C_8)$ alkyl substituted by acryloxy, methacryloxy, acrylamido or methacrylamido the molar ratio of acid to amine being from 0:1 to 10:1.

15. A method according to claim 13 wherein R is $(C_1-C_8)$ alkyl substituted by an acryloxy, methacryloxy, acrylamido or methacrylamido; $R'$ is $(C_1-C_4)$ alkyl, and $R°$ is $(C_1-C_4)$ alkyl.

16. A method according to claim 13 wherein the tertiary amine is dimethylaminoethyl acrylate, dimethylaminoethyl methacrylate, N-dimethylaminoethyl acrylamide or N-dimethylaminoethyl methacrylamide or a polymer containing units thereof.

17. A method according to claum 13 in which the reaction is conducted at a temperature in the range of from about 10° C. to 40° C.

18. A method according to claim 13 wherein R is $(C_1-C_{24})$ alkyl, allyl, benzyl, vinylbenzyl, hydroxyalkyl having 2 to 24 carbon atoms, alkoxyalkyl having 3 to 24 carbon atoms, or poly (alkoxy)alkyl having 2 to 6 oxygen atoms and 2 to 3 carbon atoms in all except one of the terminal alkyl groups, the latter having 1 to 8 carbon atoms; $R'$ is $(C_1-C_8)$ alkyl; $R°$ is $(C_1-C_8)$ alkyl, or $R'$ and $R°$ are joined together and form, with the N atom of the tertiary amine, a ring selected from morpholino, thiomorpholino, N-alkylpiperidino, or piperazino.

19. A method for producing a betaine-type product which comprises reacting at a temperature of about 0°-100° C., a mixture of acrylic acid with a polymer of tertiary aliphatic amine groups of the formula:

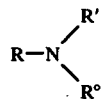

wherein R is allyl, vinylbenzyl, or $(C_1-C_8)$ alkyl substituted by an acryloxy, methacryloxy, acrylamido or methacrylamido; $R'$ is $(C_1-C_8)$ alkyl; $R°$ is $(C_1-C_8)$ alkyl or $R'$ and $R°$ may be joined together and form with the N atom of the tertiary amine, a ring selected from morpholino, thiomorpholino, N-alkylpiperidino, or piperazino.

20. A method according to claim 19 in which the reaction is effected at a temperature of about 10° C. to 40° C.

21. A method according to claim 3 wherein R is ($C_1$–$C_8$) alkyl substituted by acryloxy, methacryloxy acrylamido or methacrylamido; R' is ($C_1$–$C_4$) alkyl and R° is ($C_1$–$C_4$) alkyl.

22. The method of claim 3 in which a polymer of a tertiary aliphatic amine groups of the formula:

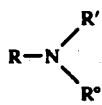

wherein R is allyl, vinylbenzyl, or ($C_1$–$C_8$) alkyl substituted by an acryloxy, methacryloxy, acrylamido or methacrylamido; R' is ($C_1$–$C_8$) alkyl; R° is ($C_1$–$C_8$) alkyl or R' and R° may be joined together and form with the N atom of the tertiary amine, a ring selected from morpholino, thiomorpholino, N-alkylpipereidino, or piperazino, is present during the reaction of the acrylic acid and the tertiary amine.

23. The method of claim 13 in which a polymer of a tertiary amine of the formula:

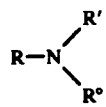

wheren R is allyl, vinylbenzyl, or ($C_1$–$C_8$) alkyl substituted by an acryloxy, methacryloxy, acrylamido or methacrylamido; R' is ($C_1$–$C_8$) alkyl; R° is ($C_1$–$C_8$) alkyl or R' and R° may be joined together and form with the N atom of the tertiary amine, a ring selected from morpholino, thiomorpholino, N-alkylpiperidino, or piperazino, is present during the reaction of the acrylic acid and the tertiary amine.

* * * * *